US 6,610,022 B1

(12) United States Patent
Ashbaugh et al.

(10) Patent No.: US 6,610,022 B1
(45) Date of Patent: Aug. 26, 2003

(54) ADJUSTABLE ORTHOPEDIC SUPPORT FASTENER SYSTEM

(76) Inventors: Terri E. Ashbaugh, 7704 Wood Bluff, San Antonio, TX (US) 78240; James M. Ashbaugh, 7704 Wood Bluff, San Antonio, TX (US) 78240

( * ) Notice: Subject to any disclaimer, the term of this patent is extended or adjusted under 35 U.S.C. 154(b) by 0 days.

(21) Appl. No.: 10/211,773

(22) Filed: Aug. 2, 2002

(51) Int. Cl.[7] .............................. A61F 5/00; A41F 9/00
(52) U.S. Cl. ........................................................ 602/19
(58) Field of Search ....................... 602/19, 5; 128/869, 128/876, 846; 2/311, 312, 321, 322; 24/306, 442, 312, 32

(56) References Cited

U.S. PATENT DOCUMENTS

| | | | | |
|---|---|---|---|---|
| 836,213 A | * | 11/1906 | Rayman ........................ 2/312 |
| 1,516,462 A | * | 11/1924 | Schvarcz ..................... 24/312 |
| 1,821,839 A | * | 9/1931 | Kerngood .................... 24/312 |
| 2,760,486 A | * | 8/1956 | Ward ........................... 602/19 |
| 4,672,720 A | * | 6/1987 | Lorenzetti ................. 24/163 R |
| 4,802,667 A | * | 2/1989 | Altner ......................... 482/93 |
| 4,930,499 A | * | 6/1990 | Rowe .......................... 602/19 |
| 5,095,894 A | | 3/1992 | Marble |
| 5,105,803 A | * | 4/1992 | Burton ........................ 602/36 |
| 5,363,863 A | * | 11/1994 | Lelli et al. .................. 128/876 |
| 5,388,274 A | * | 2/1995 | Glover et al. .................. 2/338 |
| 5,433,697 A | | 7/1995 | Cox |
| 5,437,614 A | * | 8/1995 | Grim ........................... 602/19 |
| 5,651,764 A | | 7/1997 | Chiu |
| 5,690,609 A | | 11/1997 | Heinze, III |
| 5,722,940 A | | 3/1998 | Gaylord, Jr. et al. |
| 5,840,051 A | | 11/1998 | Towsley |
| 6,099,490 A | * | 8/2000 | Turtzo ......................... 602/19 |
| 6,102,879 A | | 8/2000 | Christensen et al. |
| 6,141,835 A | * | 11/2000 | Wilson ....................... 24/68 E |
| 6,240,923 B1 | * | 6/2001 | Barrick ....................... 128/869 |

* cited by examiner

Primary Examiner—Nicholas D. Lucchesi
Assistant Examiner—Huong Q. Pham
(74) Attorney, Agent, or Firm—Jackson Walker L.L.P.

(57) ABSTRACT

A fastener system for an orthopedic device having separable, spaced apart first posterior and second anterior sections. The system uses sets of straps, complimentary clips, cooperating fixed anchor ring assemblies and pull ring assemblies to quickly ensure accurate and proper alignment of the device to the user's body.

3 Claims, 3 Drawing Sheets

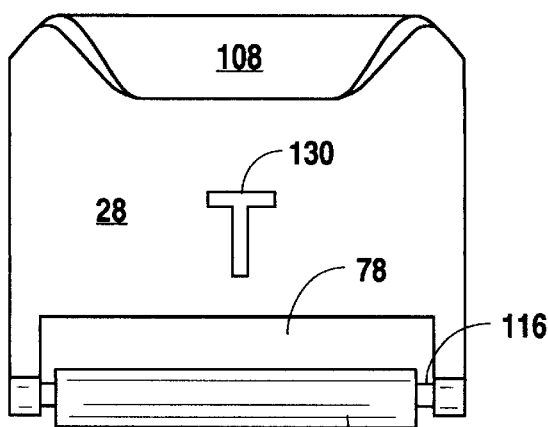
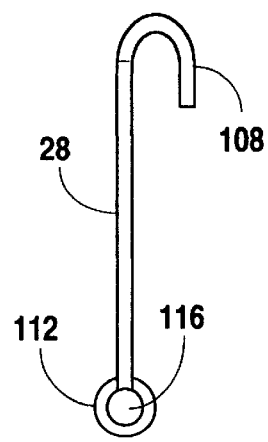
Fig. 3
Fig. 4
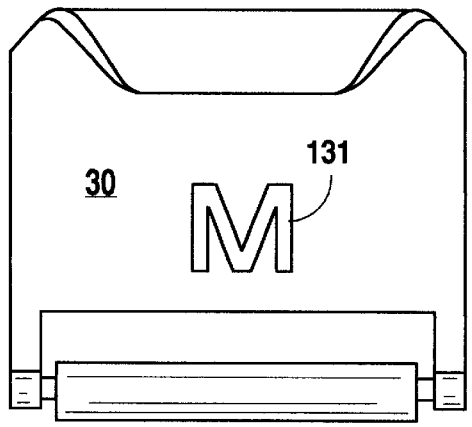
Fig. 5
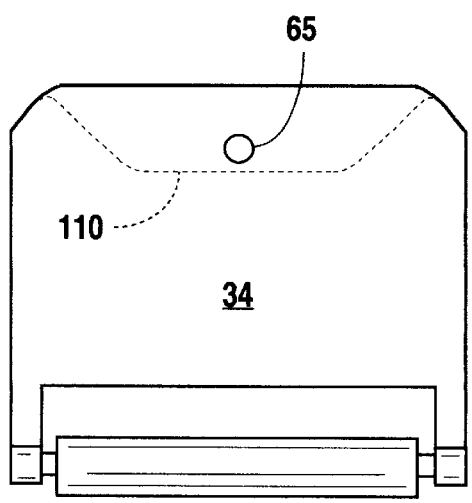
Fig. 7
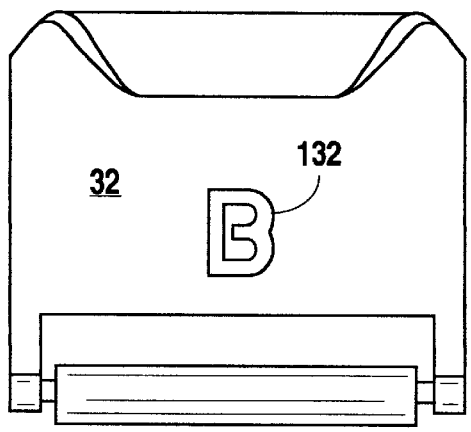
Fig. 6

ADJUSTABLE ORTHOPEDIC SUPPORT FASTENER SYSTEM

BACKGROUND OF THE INVENTION

This invention relates to an improved orthotic appliance and, more particularly, to a brace or support device for a limb wherein the device is secured to the patient with a quick fastening system. The quick clip system of the present invention provides an apparatus for attaching a back support appliance without twisting the patient's limb, torso, or trunk.

As is well known, many orthotic appliances must be frequently removed by the patient throughout an ordinary day. When the patient's movement and flexibility are impaired or restricted by the physician's directive, the process of removing and reinstalling the appliance can be quite difficult. Existing devices require elaborate procedures for securing an orthopedic device to a patient. Orthosis manufacturers prepare extensive, detailed diagrams to facilitate instructing and training physicians, nurses, therapists, and patients in the proper procedures for attaching such devices. These procedures are even more difficult when the appliance is a rigid, molded, conformable, corset-like lumbosacral spine and pelvic tilt control brace and the patient must not twist his/her back, trunk or torso. The present invention utilizes a unique, easy-to-adjust fastening system to secure the orthopedic appliance to the patient. The present system may be utilized with any two piece, separable appliance having a front (anterior) section and a back (posterior) section wherein the appliance is secured to the patient's body by adjustable straps.

Numerous prior art fastener systems are known. These include U.S. Pat. Nos. 6,102,879; 5,840,051; 5,722,940; 5,690,609; 5,651,764; 5,433,697; 5,363,863; and 5,095,894. However, none of the prior art teaches or discloses the unique quick clip system of the present invention.

BRIEF DESCRIPTION OF THE DRAWINGS

FIG. 3 is a front elevation view of a clip of the present invention with a first indicia of strap position of a clip body.

FIG. 4 illustrates a side elevation view of a clip of the present invention.

FIG. 5 shows a front elevation view of a second clip of the present invention with a second strap position indicator shown on the clip.

FIG. 6 is a front elevation view of a third clip of the present invention with yet another strap position indicator.

FIG. 7 illustrates a back elevation view of a clip of the present invention with a locking member hole in the hook section.

DETAILED DESCRIPTION OF THE PREFERRED EMBODIMENT

Figure 1:
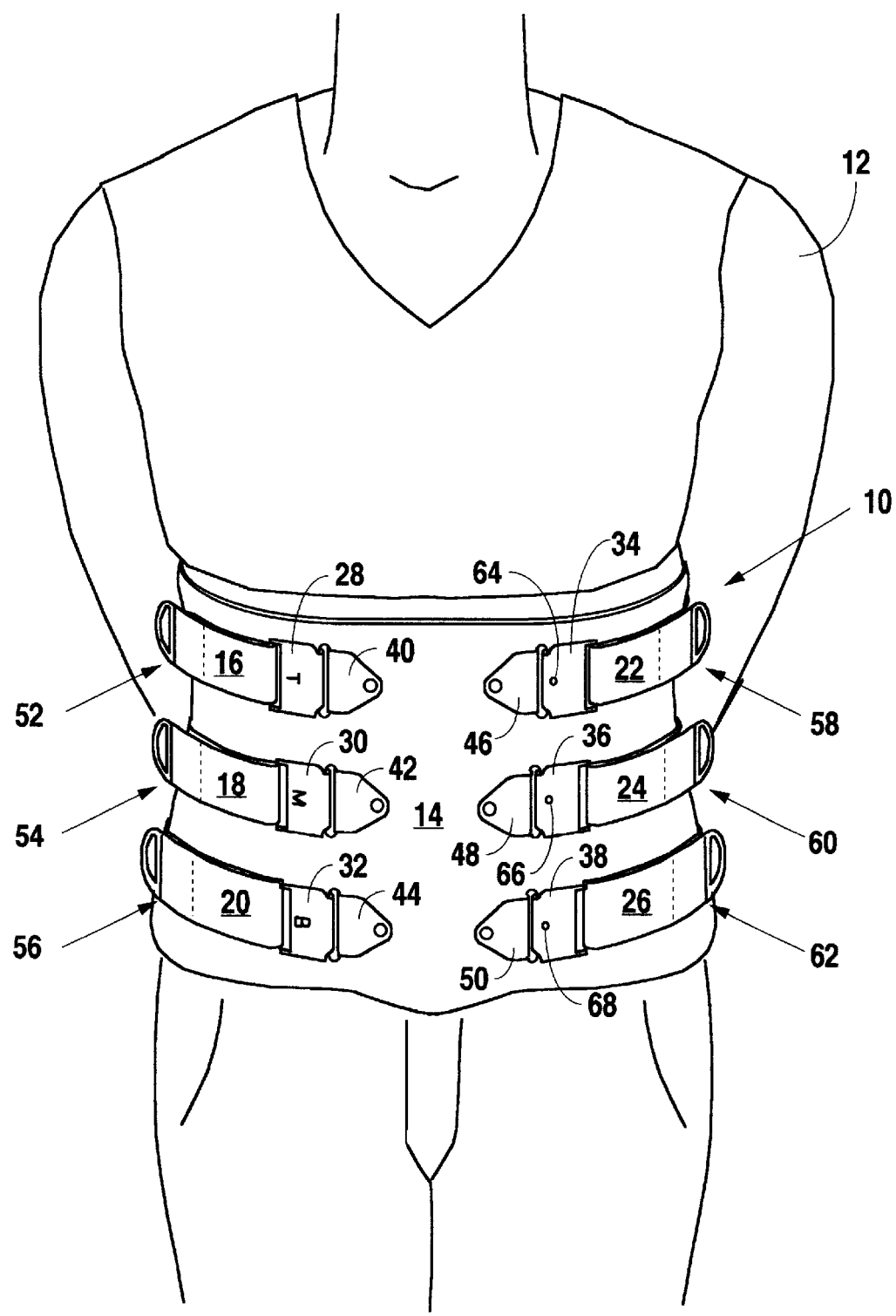
FIG. 1 illustrates a front perspective view of an orthopedic device having the present inventive fastener system.

In FIG. 1, a rigid, molded plastic torso brace (10) incorporating the present invention is shown properly fitted and secured to a patient (12). The front (14) (anterior) and back (posterior) sections of the brace are sized and shaped to generally conform to the patient's skeletal structure. While the drawings illustrate the present invention in the form of an orthopedic back brace structure (10), it should be understood that the present invention may also be incorporated in any two-piece, separable support appliance that requires adjustment of straps to secure the appliance to the patient; for example, an arm, shoulder, leg, hip, wrist, or ankle brace may be adapted to accept the present fastener system. The improvement lies in the ease of proper alignment and adjustment of the appliance to the patient's body without undue twisting or turning.

Brace (10) is shown with six securing straps (16, 18, 20, 22, 24 and 26), six complimentary clips (28, 30, 32, 34, 36 and 38), six cooperating fixed anchor ring assemblies (40, 42, 44, 46, 48 and 50), and six releasably attachable pull ring assemblies (52, 54, 56, 58, 60 and 62). Again, it should be understood that more or less of these elements may be required depending on the size and shape of the appliance. However, the straps, clips, anchor ring assemblies, and pull ring assemblies are used in cooperating sets to achieve the desired results.

In FIG. 1, clips 34, 36 and 38 are provided with locking set screws (64, 66 and 68) as will as described in more detail below.

Figure 2:
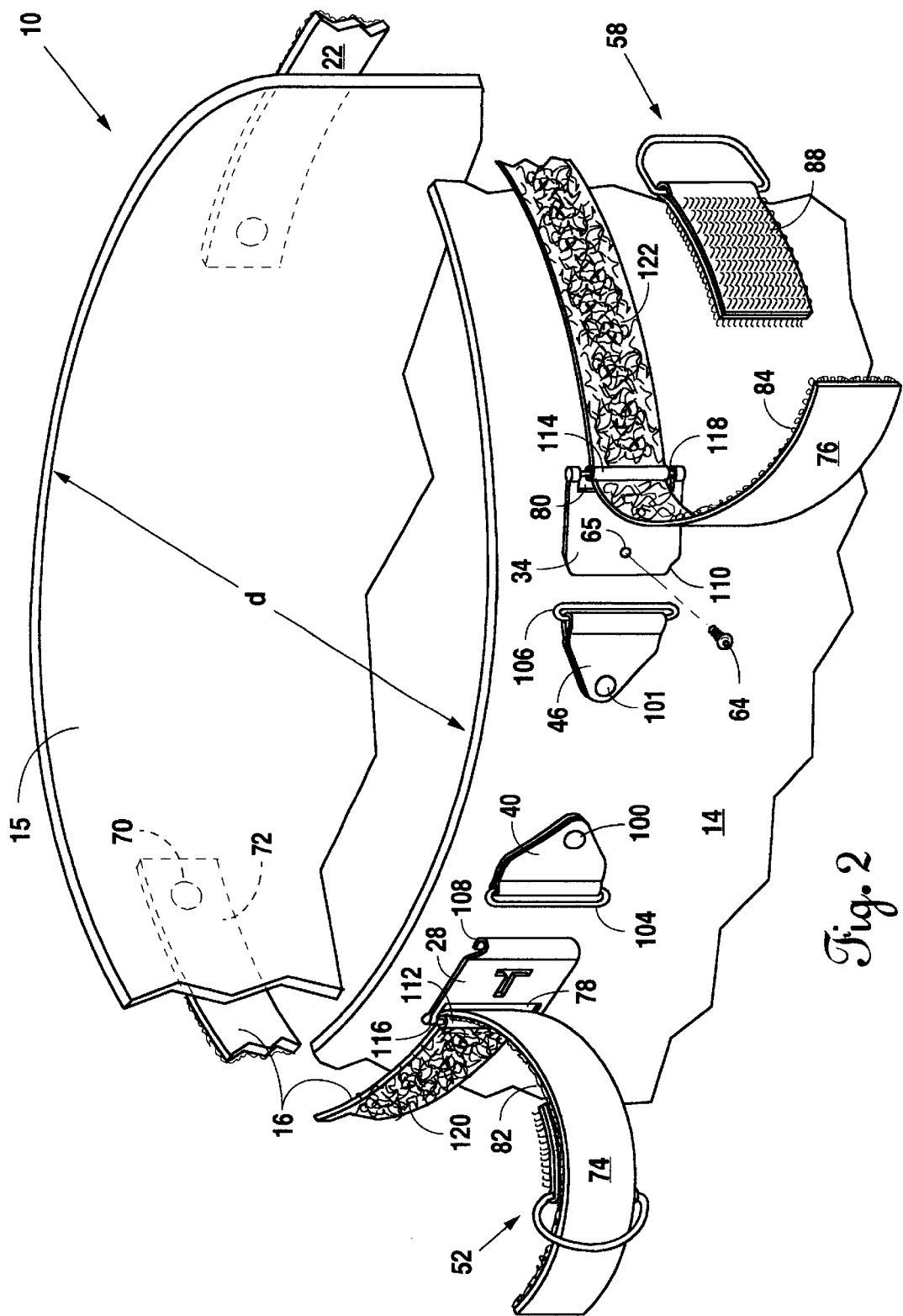
FIG. 2 shows a partial exploded perspective view of a strap and clip arrangement of the present inventive system.

Turning to FIG. 2, the top set of fasteners is illustrated for clarity purposes. The top right securing strap (16) is permanently secured at a first end (72) by a rivet, screw, or like fastener to the posterior brace section (15). Cooperating and opposing, top left side securing strap (22) is likewise permanently fastened to the posterior brace section (15). Each strap (16 and 22) extends from the back side (15) to the front side (14) of the brace (10). The lengths of the straps is adjustable to vary the distance separating the brace sections to accommodate the body size of the patient. Once the strap lengths are properly set, there is little or no need to frequently readjust the strap lengths except to extend the length to fit over differing clothing thicknesses, or if there has been a significant limb or body size change.

The straps (16 and 22) are wrapped forwardly around the outer surface of the brace sections and second ends (74 and 76) are threaded through fastener loops (78 and 80) in clips (28 and 34), respectively. The straps have appropriate facings (82 and 84) to attach Velcro (hook and loop fastener) sections (86 and 88) on pull ring assemblies (52 and 58), as will be well understood by one of ordinary skill in the art. Once the ends (74 and 76) are threaded and pull rings (90 and 92) are attached, the length of the straps may be adjusted to set the distance d between the brace sections (14 and 15).

The clips (28 and 34) are connectable to anchor ring assemblies (40 and 46), which are permanently attached to the anterior brace section (14) by fasteners (100 and 101), through fastener loops (104 and 106). The C-shaped hooks (108 and 110) hook about the loops (104 and 106).

To adjust the strap lengths, the user pulls the pull rings (90 and 92) causing the straps to slide over sleeves (112 and 114) which rotate about fixed journals (116 and 118) in the strap loops (78 and 80) in clips (28 and 34, respectively). The rotatable sleeves (112 and 114) facilitate the adjusting of the straps and reduces wear on the strap surfaces. These features are particularly important when adjusting the straps must be accomplished without twisting or turning the torso or limb. As the appropriate length is achieved, the pull rings are pressed against intermediate sections (120 and 122) of the straps, thereby securing the straps to the hook and loop fastener sections (86 and 88).

To reduce the number of straps which must be adjusted, selected clips (34, 36 and 38) are provided with locking set screws (64, 66 and 68) which pass through threaded holes (65) (in FIG. 2) to the C-shaped end of the clips. Tightening the set screw keeps the hook (110) on the clip (34) from disconnecting from the loop (106).

When the user must remove the appliance (10), all he/she has to do is loosen the pull ring assemblies (52, 54 and 56) on one side from the intermediate sections and the two separate brace sections (14 and 15) may be separated as the clips (28, 30 and 32) are released from anchor ring assemblies (40, 42 and 44). When the appliance is to be reapplied the user reverses the process. All adjustment takes place in the front of the appliance and can be seen by the user with no twisting or turning required.

To further eliminate the need to twist and turn, selected clips (28, 30 and 32) are provided with indicia (130) on other selected clips to indicate the relative position of the strap on the posterior brace section. For example, FIGS. 3, 5 and 6 show indicia (130, 131 and 132) indicating that clips (28, 30 and 32) are the "top," "middle," and "bottom" straps. The user does not have to twist around to make sure that the straps are not crossed. While one embodiment uses indicia actually cut through the clip body, it should be understood that the indicia may be stamped, raised, or printed on the selected clips.

Although the invention has been described with reference to a specific embodiment, this description is not meant to be construed in a limiting sense. On the contrary, various modifications of the disclosed embodiments will become apparent to those skilled in the art upon reference to the description of the invention. It is therefore contemplated that the appended claims will cover such modifications, alternatives, and equivalents that fall within the true spirit and scope of the invention.

What is claimed is:

1. A fastener system for an orthopedic device comprising:

separable, spaced apart first posterior and second anterior brace sections, a plurality of securing straps permanently secured at first ends to said first posterior brace section and extensible to said second anterior brace section, said straps having lengths adjustable to vary the distance separating said brace sections;

a complimentary clip attached to a second end of each of said plurality of straps, each of said clips further comprising:

a C-shaped hook on a first end of said clip and a strap loop on a second end of said clip, said strap loop having a fixed journal with a sleeve rotatably affixed over said fixed journal;

a cooperating fixed anchor ring assembly for each of said complimentary clips, each of said anchor ring assemblies permanently attached at a first end to said second anterior brace section and having a fastener loop on a second end, each of said fastener loops cooperating with a respective one of said C-shaped hooks on said clips to connect said clips to said anchor ring assemblies; and a plurality of pull ring assemblies releasably attachable to each of said second ends of said plurality of securing straps and further releasably attachable to an intermediate section of each of said plurality of securing straps.

2. The fastener system of claim 1 wherein first selected ones of said clips further comprise a locking member to lock said first selected clips to first selected cooperating fixed anchor ring assemblies.

3. The fastener system of claim 1 wherein second selected ones of said clips further comprise indicia thereon indicating the relative position of selected ones of said permanently secured first ends of said straps on the first posterior brace section.

* * * * *